United States Patent [19]

Wright

[11] 4,272,525
[45] Jun. 9, 1981

[54] DERIVATIVES OF POLYENE MACROLIDE ANTIBIOTICS CONTAINING AN AMINO SUGAR MOIETY, PROCESS FOR THE PREPARATION THEREOF, AND PHARMACEUTICAL COMPOSITIONS CONTAINING THEM

[75] Inventor: John J. Wright, Cedar Grove, N.J.

[73] Assignee: Schering Corporation, Kenilworth, N.J.

[21] Appl. No.: 128,011

[22] Filed: Mar. 7, 1980

Related U.S. Application Data

[63] Continuation-in-part of Ser. No. 953,824, Oct. 23, 1978, abandoned.

[51] Int. Cl.³ .................... A61K 37/00; A61K 31/70; C07C 103/52; C07H 19/16
[52] U.S. Cl. .................... 424/177; 424/180; 424/181; 260/112.5 R; 536/17 R
[58] Field of Search .................... 424/177, 180, 181; 536/17 R, 9; 260/112.5 R

[56] References Cited

U.S. PATENT DOCUMENTS 4,035,567  7/1977  Sipos ..................... 536/4

OTHER PUBLICATIONS

Chemical Abstract, vol. 77, 1972, p. 36, Abst. No. 97013g, Mechlinski et al., "Polyene macrolide derivatives, I. N.-acylation and esterification reaction with amphotericin B".
Chemical Abstracts, vol. 80, 1974, p. 471, Abst. No. 121291f, Ferrari et al., "Alkyl esters of polyene antibiotics".

Primary Examiner—Delbert R. Phillips
Assistant Examiner—Blondel Hazel
Attorney, Agent, or Firm—Elizabeth A. Bellamy; Mary S. King; Anita W. Magatti

[57] ABSTRACT

This invention relates to derivatives of polyene macrolide antibiotics containing an amino sugar moiety, the process for their preparation and pharmaceutical compositions containing them useful in the treatment of fungal infections.

30 Claims, No Drawings

DERIVATIVES OF POLYENE MACROLIDE ANTIBIOTICS CONTAINING AN AMINO SUGAR MOIETY, PROCESS FOR THE PREPARATION THEREOF, AND PHARMACEUTICAL COMPOSITIONS CONTAINING THEM

CROSS-REFERENCE TO RELATED APPLICATIONS

This application is a continuation-in-part of copending application Ser. No. 953,824 filed Oct. 23, 1978 now abandoned.

This invention relates to derivatives of polyene macrolide antibiotics containing an amino sugar moiety, process for the preparation thereof, and pharmaceutical compositions containing them. It has been established that compounds of this invention show antifungal activity and are useful in the treatment of fungal infections.

Polyene macrolide antibiotics containing an amino sugar moiety are known in the art. In general, they are useful in the treatment of mycosis, benign prostatic hypertrophy and elevated blood cholesterol. Among the known polyene macrolides there are four antibiotics that are used as anti-fungal agents in the United States; these are amphotericin B, candicidin, pimaricin and nystatin. The agent most commonly known or used is amphotericin B as the sodium desoxycholate complex, which is known as FUNGIZONE ®.

Other polyene macrolides have received varying amounts of attention by research workers in this country, however, their general lack of water solubility, their poor stability, and their toxic properties have contributed to their failure to achieve an important place in therapy. Attempts have been made to improve the usefulness of amphotericin B. Straight chain alkyl esters of amphotericin B and a number of other polyenes have been reported. The reports indicate that these esters and their salts have been generally found to have reduced toxicity relative to their parent polyenes, but they have also been found to be less active. N-Acyl derivatives of these compounds have also been prepared and, again, although they have been found to be less toxic than their parent polyenes, they have also been found to be less potent. N-Glycosyl derivatives of certain polyenes have also been reported and these appear to be equipotent or more potent than their parents and about as toxic. Overall then there is, therefore, a need for a less toxic but potent systemic anti-fungal agent.

The novel compounds of this invention are the derivatives of polyene macrolide antibiotics of the general formula

wherein M is a polyene macrolide antibiotic moiety containing an amino sugar moiety, the amino group of which is substituted by X, wherein X is

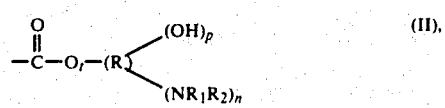

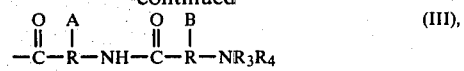

—$R_5$ or hydrogen, wherein A and B independently of each other are hydrogen or $NR_3R_4$ or one of A and B is hydrogen and the other is

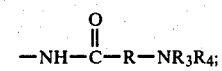

R is a saturated hydrocarbon group having 1 to 10 carbon atoms; $R_1$ and $R_2$ independently of each other are hydrogen or a straight chain alkyl group having 1 to 3 carbon atoms or one of $R_1$ and $R_2$ is hydrogen and the other a straight chain alkyl group having 1 to 3 carbon atoms substituted by an $NH_2$ group; $R_3$ and $R_4$ independently of each other are hydrogen or a straight chain alkyl group containing 1 to 3 carbon atoms; $R_5$ is histidyl, tyrosyl, tryptophyl, arginyl, phenylalanyl or prolyl or an $(\alpha)$-N-[$(NH_2)_m$(-R-)CO]-derivative of histidyl, tyrosyl, tryptophyl, phenylalanyl or prolyl; m is 1 or 2; n is 1 to 3, t is zero or 1, and when t is zero p is zero to 4 and when t is 1 p is zero; with the proviso that not more than one hetero atom is attached to the same carbon atom in any one of R, $R_1$ and $R_2$ and that in those compounds containing more than one R-group, these R-groups may be of the same or different chain length; z is zero or 1, and Y is hydrogen, an alkyl group containing 1 to 10 carbon atoms, allyl, propargyl, benzyl or phenylpropargyl, with the proviso that, when X is hydrogen, z must be 1 and Y must be allyl, propargyl, benzyl or phenylpropargyl; and the pharmaceutically acceptable acid addition salts of all the foregoing compounds. Preferably these derivatives are derived from a polyene macrolide antibiotic of the general formula

wherein z is zero or 1, which antibiotic of Formula IV is amphotericin B, ascocin, aureofacin, aureofungin A, aureofungin B, candicidin, candidin, eurotin A, flavomycin, fulvomicin A, fulvomicin B, fulvomicin C, fungimycin, hamycin A, leucensomycin, levorin, mycoheptin, nystatin A, partricin, pimaricin, polyfungin, rimocidin, trichomycin A, vacidin A, DJ-400 $B_1$, DJ-400 $B_2$, 67-121A, 67-121B, 67-121C, PA 150, PA 616, or 2814 H, of which pimaricin and 67-121C and especially amphotericin B are most preferred. The amino sugar moiety most generally is mycosamine but in at least one instance is perosamine. Some of the polyene macrolide antibiotics contain aromatic moieties on the macrolide ring and these aromatic rings may also contain an amine group; however, under the reaction conditions of this invention, these amine groups are not involved.

As stated before R is a saturated hydrocarbon having 1 to 10 carbon atoms, said hydrocarbon may be a straight or branched chain alkylene group, such as for example methylene, ethylene, n-propylene, isopropylene, n-butylene, isobutylene, tert.-butylene, $\beta$-methylpropylene, pentylene, hexylene, heptylene, octylene, nonylene, decylene and the like.

Preferably R is a straight chain alkylene group especially a group containing 1 to 5 carbon atoms.

Those derivatives are preferred wherein X is $$-\overset{O}{\underset{\|}{C}}-(R)_{z}-(NR_1R_2)_n \quad (V),$$

wherein n is 1 or preferably 2 and R, $R_1$ and $R_2$ are as defined above.

Preferred are those derivatives wherein $R_1$, $R_2$, $R_3$ and $R_4$ are hydrogen, and, provided that the compound contains two $NH_2$ groups one of the amino groups is terminal.

As is apparent from the above, substituent X (formula I) may consist of one, two or three aminoacyl groups, preferably alanyl, glycyl, histidyl, tryptophyl, isoleucyl, leucyl, lysyl, norvalyl, ornithyl, phenylalanyl, prolyl, seryl, tyrosyl or valyl. X may contain identical or different amino acyl groups, so that X is glycyl-glycyl, glycyl-lysyl, leucyl-leucyl, alanyl-lysyl, histidyl-lysyl, and the like.

Preferably X is lysyl or ornithyl.

In those instances where the group X has one or more chiral centers, the diastereomeric derivatives of formula I may be used separately or in admixture. For example, the nature of the synthesis may result in formation of a N-[D]-lysyl, a N-[L]-lysyl, or a N-[D,L]-lysyl amphotericin B, the latter being an equal mixture of the first two.

Derivatives of polyene macrolide antibiotics containing a carboxylic acid function (i.e. compounds of formula I wherein z is 1) are preferred in the form of their esters. Derivatives are preferred wherein Y is an alkyl group containing 1 to 4 carbon atoms, especially those wherein Y is methyl. Also the novel esters of formula I, wherein X is hydrogen, z is one and Y is allyl, benzyl, propargyl or phenylpropargyl are of interest.

The pharmaceutically acceptable acid addition salts of this invention can be derived from inorganic acids, such as for example hydrochloric, sulfuric, and phosphoric acid, or from organic acids such as for example formic, maleic and tartaric acid. The physical embodiments of the salts are characterized by being colorless to yellow/orange solids (dependent on the degree of unsaturation of the polyene) which are soluble in water, sparingly soluble in most polar organic solvents and insoluble in most non-polar organic solvents.

Of the compounds of this invention the following are of great interest:

N-D-lysyl amphotericin B methyl ester dihydrochloride, N-D-ornithyl amphotericin B methyl ester dihydrochloride, N-D-lysyl pimaricin methyl ester dihydrochloride, N-glycyl 67-121C, N-glycyl amphotericin B methyl ester hydrochloride, N-D-2,4-diaminobutyryl amphotericin B methyl ester dihydrochloride, N-β-alanyl amphotericin B methyl ester hydrochloride, N-(aminoethylglycyl) amphotericin B hydrochloride, N-(aminoethylglycyl) amphotericin B methyl ester dihydrochloride, N-D-lysyl amphotericin B hydrochloride, N-L-lysyl amphotericin B hydrochloride, N-L-lysyl amphotericin B methyl ester dihydrochloride, N-L-ornithyl amphotericin B methyl ester dihydrochloride, N-D-ornithyl amphotericin B propargyl ester dihydrochloride, N-(2-aminoethoxycarbonyl) amphotericin B methyl ester hydrochloride, N-L-histidyl amphotericin B methyl ester dihydrochloride, amphotericin B allyl ester hydrochloride, amphotericin B propargyl ester hydrochloride, amphotericin B (3-phenyl-2-propynyl) ester hydrochloride, N-D-lysyl amphotericin B propargyl ester dihydrochloride, N-histidyl-lysyl amphotericin B methyl ester hydrochloride, N-D-ornithyl-amphotericin B hydrochloride, and N-L-ornithyl amphotericin B hydrochloride.

The compounds of this invention are useful in the treatment of mycosis, benign prostatic hypertrophy and elevated blood cholesterol, as are the known polyene macrolide antibiotics. The compounds of this invention are especially useful as anti-fungal agents. Surprisingly, in tests compounds of this invention have shown to be less toxic and more active as anti-fungal agents than the respective known polyene macrolide antibiotics.

The compounds of this invention thus can be used to effectively combat fungus infections of the following species: *Histoplasma capsulatum, Coccidiodes immitis,* Candida spp., *Blastomyces dermatitidis,* Rhodotorula, *Cryptococcus neoformans, Sporotrichum schenckii, Mucor mucedo, Aspergillus fumigatus,* Trichophyton spp., Microsporum spp. and Epidermophyton. Additionally, the compounds have been found to be active fungicidally rather than fungistatically.

In general, the compounds of this invention and their pharmaceutically acceptable acid addition salts may be administered orally, e.g. compounded in the form of tablets, capsules, elixirs or the like, or they may be applied topically, e.g. in the form of ointments, lotions, creams or gels. Preferentially, they may be administered parenterally via intramuscular, intravenous, subcutaneous, intralesional and intrasternal injection. The injectable solution will usually be administered at from about 1 mg to 5 mgs of compound per kilogram of body weight per day. Pharmaceutical carriers useful in the preparation of the foregoing formulations will include, for example, such substances as water, oils, fats, waxes, polyesters, alcohols, polyols and the like.

The present invention includes within its scope the method for treating fungal infections which comprises administering to a mammal infected with a susceptible fungus a non-toxic fungicidally effective amount of a compound of this invention. Also included within the inventive concept are pharmaceutical compositions comprising a non-toxic, fungicidally effective amount of a compound of this invention together with a non-toxic, pharmaceutically acceptable carrier.

The compounds of this invention can be prepared according to known methods, especially according to methods known from peptide synthesis. In these methods the polyene macrolide antibiotics containing an aminosugar moiety are used as starting material, especially amphotericin B, ascocin, aureofacin, aureofungin A, aureofungin B, candicidin, candidin, eurotin A, flavomycin, fulvomicin A, fulvomicin B, fulvomicin C, fungimycin, hamycin A, leucensomycin, levorin, mycoheptin, nystatin A, partricin, pimaricin, polyfungin, rimocidin, trichomycin A, vacidin A, DJ-400 $B_1$, DJ-400 $B_2$, 67-121A, 67-121B, 67-121C, PA 150, PA 616 and 2814H.

The polyene macrolides are highly insoluble compounds so that when they are reacted with other compounds, various polar solvents must be used as, for example, dimethylformamide, dimethylsulfoxide, and hexamethylphosphorictriamide. In reactions wherein acylation of the polyene's hydroxyl group(s) has to be prevented a small amount of methanol to any of the polar solvents is usually added.

A. For the preparation of derivatives of polyene macrolide antibiotics of the general formula

 (I), wherein M is a polyene macrolide antibiotic moiety containing an amino sugar moiety, the amino group of which is substituted by X, wherein X is

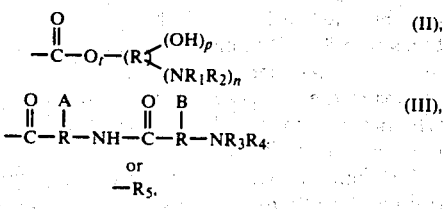

wherein A and B independently of each other are hydrogen or $NR_3R_4$ or one of A and B is hydrogen and the other is

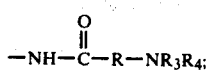

R is a saturated hydrocarbon group having 1 to 10 carbon atoms; $R_1$ and $R_2$ independently of each other are hydrogen or a straight chain alkyl group having 1 to 3 carbon atoms or one of $R_1$ and $R_2$ is hydrogen and the other a straight chain alkyl group having 1 to 3 carbon atoms substituted by an $NH_2$ group; $R_3$ and $R_4$ independently of each other are hydrogen or a straight chain alkyl group containing 1 to 3 carbon atoms; $R_5$ is histidyl, tyrosyl, tryptophyl, arginyl, phenylalanyl or prolyl or an ($\alpha$)-N-[$(NH_2)_m$+R→CO]-derivative of histidyl, tyrosyl, tryptophyl, phenylalanyl or prolyl; m is 1 or 2; n is 1 to 3, t is zero or 1, and when t is zero p is zero to 4 and when t is 1 p is zero; with the proviso that not more than one hetero atom is attached to the same carbon atom in any one of R, $R_1$ and $R_2$ and that in those compounds containing more than one R-group, these R-groups may be of the same or different chain length; z is zero or 1, and Y is hydrogen, an alkyl group containing 1 to 10 carbon atoms, allyl, propargyl, benzyl or phenylpropargyl, a polyene macrolide antibiotic of the general formula

 (VI), wherein M, Y and z are as defined above, is reacted with a reactive derivative of a compound of the general formula HOX' (VII), wherein X' is defined as group X above with the exception that the amino groups contained therein are protected. This reaction is followed by the removal of the protecting group(s) and, if desired, esterification of compounds containing a carboxy group. For the preparation of compounds containing an esterified carboxy group it is preferred, however, to carry out the said esterification before removing the protecting group(s).

The process may be outlined by the following reaction scheme:

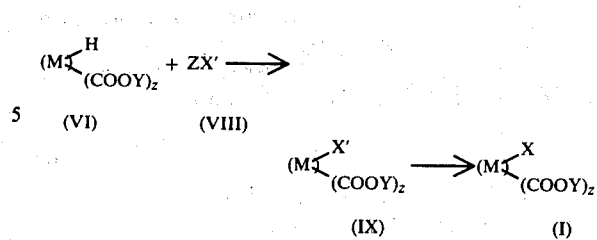

In the formulae of this reaction scheme M, Y, z and X' are as defined above and Z is an eliminatable group, such as for example N-hydroxysuccinimidyl, N-hydroxyphthalimidyl or an acyl imidazolyl. Preferably Z is N-hydroxysuccinimidyl.

The amino groups contained in compound ZX' are protected by easily removable groups, such as for example trifluoroacetyl, 2,2,2-trichloroethoxycarbonyl and fluorenemethoxycarbonyl, the latter group being preferred.

The reaction of the compounds of formula VI and VIII is carried out in a polar organic solvent such as dimethylformamide, dimethylsulfoxide, hexamethylphosphoric triamide or mixtures of these solvents. In reactions wherein acylation of possible hydroxyl group(s) of the polyene has to be prevented a small amount of methanol can be added. Several other means can be used to support this reaction, such as performing the reaction under nitrogen and/or addition of triethylamine.

The compound ZX' can be prepared by known methods. For the preparation of compounds of formula I wherein X is the group

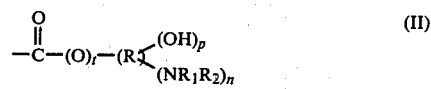 (II)

wherein t is one, p is zero and R, $R_1$, $R_2$ and n are as defined above, ZX' (VIII) can be prepared by reacting an appropriate N-protected aminoalkanol with phosgene and then with preferably N-hydroxysuccinimide. For the preparation of all other compounds of formula I ZX' can be prepared by reacting the appropriate N-protected amino acid with preferably N-hydroxysuccinimide and dicyclohexylcarbodiimide.

The reaction conditions under which the protecting groups of the amino groups are removed in this process are known in the art and depend on the kind of protecting group.

Compounds of formula I and IX containing a free carboxy group, (wherein z is one and Y is hydrogen) can be esterified by reaction with a reactive derivative of the appropriate hydrocarbon. The compounds of formula I, which are compounds with at least one free amino group, can be esterified for example by reaction with the appropriate diazo derivative of the hydrocarbon such as diazomethane, diazoethane, diazopropane or diazobutane (e.g. as described in U.S. Pat. Nos. 3,936,526 and 4,038,382). The compounds of formula IX, which are compounds containing one or more protected amino groups can be reacted with alkylating agents such as for example methyl iodide, methyltosylate, ethyliodide, or with allyliodide, propargyl bromide methyl sulfate and phenylpropargyl bromide. In this alkylation reaction it is preferred to use compounds of formula IX wherein the amino group(s) is (are) protected by fluorenemethyloxycarbonyl.

B. For the preparation of a derivative of a polyene macrolide antibiotic of the general formula

wherein M is a polyene macrolide antibiotic moiety containing an amino sugar moiety, the amino group of which is substituted by X, wherein X is $$-CO-CH_2-NHR_1 \qquad (X),$$

wherein $R_1$ is hydrogen, or a straight chain alykl group having 1 to 3 carbon atoms which may be substituted by an $NH_2$ group; z is zero or 1, and Y is hydrogen, an alkyl group containing 1 to 10 carbon atoms, allyl, propargyl, benzyl or phenylpropargyl; a N-iodoacetyl derivative of the polyene macrolide antibiotic is reacted with an amine of the general formula $H_2NR_1$ (XI), wherein $R_1$ is as defined above and, if desired, esterified, provided the macrolide contains a carboxy group. The reaction is carried out in a polar solvent such as for example dimethylformamide, dimethylsulfoxide and hexamethylphosphorictriamide. Methanol may be added to the solvent. By this process derivatives such as for example the N-glycyl, N-methylglycyl and N-aminoethylglycyl derivatives of the polyene macrolide antibiotics can be prepared. The so obtained compounds can be esterified as described in process A.

The N-iodoacetyl derivatives of the polyene macrolide antibiotics can be prepared by reacting the relevant macrolide with iodoacetic anhydride in a polar solvent.

C. For the preparation of derivatives of polyene macrolide antibiotics of the general formula

wherein X is as previously defined, z is one, Y is an alkyl group containing 1–10 carbon atoms, allyl, propargyl, benzyl or phenylpropargyl and M is as defined above, an appropriate polyene macrolide antibiotic which contains a carboxy group is esterified.

The preferred process for the preparation of these compounds is a novel process. In this process the carboxylic acid moiety of the polyene macrolide antibiotic, wherein the amino groups in X have been protected, in the instance wherein X is hydrogen the amino group of the amino sugar moiety is protected by treatment with an excess of an aromatic aldehyde, is reacted with a reactive derivative of the relevant hydrocarbon and an excess of a tertiary amine. Preferably, the reaction is carried out in a polar solvent such as for example hexamethylphosphorictriamide, dimethylsulfoxide or dimethylformamide wherein the macrolide is soluble. As soon as the reaction is finished any protecting group is removed and the desired ester of the polyene macrolide antibiotic is isolated.

Aromatic aldehydes suitable for the above reaction are for example paramethoxybenzaldehyde, paranitrobenzaldehyde, salicylaldehyde, and benzaldehyde. As reactive derivatives of the relevant hydrocarbons (alkanes, propene, propyne, phenylpropyne and toluene) can be used, their bromides, iodides and the like.

The reactive derivatives may be exemplified by methyl iodide, ethyl iodide, allyl iodide, propargyl bromide, methyl sulfate and phenylpropargyl bromide.

The so obtained products may be subjected to subsequent treatment such as transformation into the pharmaceutically acceptable acid addition salt. The salts are made according to known procedures such as by neutralizing the free base with the appropriate acid, usually to about pH 5. The acid addition salts may be mono- or di- in nature depending on the number of free amine groups in the compound, the amount of acid used and whether or not the carboxy group possibly contained in the base is esterified.

The following Examples and Formulations are illustrative of methods whereby the compounds of my invention can be prepared and the pharmaceutical compositions in which they may be administered, it being understood that the invention is not to be limited thereby.

EXAMPLE 1

N-(2-Aminoethoxycarbonyl)Amphotericin B

A. N-Trifluoroacetyl-Ethanolamine

Ethanolamine (12 g) is dissolved in methanol (50 ml) and S-ethylthiotrifluoroacetate (35 g) is added dropwise. The reaction is permitted to stand overnight irrigated with a stream of argon to remove ethanethiol. The excess solvent is removed in vacuo to leave the title product.

B. 2-N-Trifluoroacetylaminoethoxycarbonyloxy Succinimide

N-Trifluoroacetyl-ethanolamine (7.8 g) in dichloromethane (100 ml) is treated with phosgene (15 g) in dichloromethane (120 ml). Triethylamine (6 ml) is added dropwise with stirring.

After four hours at room temperature excess phosgene is removed by the rapid passage of nitrogen and the solution is filtered and the solvent removed in vacuo. The residue is dissolved in dichloromethane (100 ml) and N-hydroxysuccinimide (5.8 g) and pyridine (12 g) are added. After 18 hours the solvent is removed under vacuum to provide the named compound as a residue which is used without further purification.

C. N-(2-N'-Trifluoroacetylaminoethoxycarbonyl) Amphotericin B

Amphotericin B (2 g) in 27.5 ml of a 9:1 dimethylsulfoxide:methanol mixture is treated with 2-N-trifluoroacetylaminoethoxycarbonyloxysuccinimide (3.9 g) dissolved in a minimum amount of tetrahydrofuran, added in portions over 7.5 hours. Triethylamine (327 mg) is added and the mixture is stirred for 2.5 hours. The mixture is then diluted with 25 ml of methanol and added dropwise to 600 ml of ether. Filtration of the yellow precipitate, washing with ether and drying gives the named compound: $\nu$max (KBr) 1715 cm$^{-1}$; $\lambda$max. (20% aqueous tetrahydrofuran), 348 nm ($E_{1\%}^1$=263), 367 nm ($E_{1\%}^1$=563), 386 nm ($E_{1\%}^1$=946), 410 nm ($E_{1\%}^1$=1056).

D. N-(2-Aminoethoxycarbonyl)Amphotericin B

N-(2-N'-trifluoroacetylaminoethoxycarbonyl)amphotericin B (1.985 g) in 60 ml of a 1:1 dimethylformamide:concentrated ammonium hydroxide mixture is stirred 9.5 hours with monitoring by thin layer chromatography (2:2:1 chloroform:methanol:water, lower phase). Dilution with 60 ml methanol and dropwise addition to excess ether yields a yellow precipitate which is filtered, washed with ether and dried. The precipitate is dissolved in 10 ml dimethylsulfoxide and chromatographed on 250 g SiO$_2$ eluted with the lower phase of a 2:2:1 chloroform:methanol:water mixture, to obtain the title compound: $[\alpha]_D^{26}+213.6°$ (DMSO); λmax (20% aqueous tetrahydrofuran) 348 nm ($E_{1\%}^1=310$), 367 nm ($E_{1\%}^1=680$), 386 nm ($E_{1\%}^1=1140$), 410 nm ($E_{1\%}^1=1270$).

EXAMPLE 2

N-Glycyl Amphotericin B Methyl Ester Hydrochloride

A. N-Trifluoroacetylglycyloxy Succinimide

N-Trifluoroacetylglycine (684 mg) and N-hydroxysuccinimide (480 mg) in 5 ml of dry CH$_2$Cl$_2$ at 50° C. are treated with a solution of 915 mg dicyclohexylcarbodiimide (4.43 mmol) in 5 ml of CH$_2$Cl$_2$. The mixture is stirred at room temperature overnight, is then filtered and evaporated to produce the named compound which can be used in subsequent reactions without further purification.

B. N-(N'-Trifluoroacetylglycyl)Amphotericin B

Amphotericin B (500 mg) in 5.5 ml 9:1 dimethylsulfoxide:methanol with 246 mg of the product of step A is stirred at 25° C. for three hours. The mixture is diluted with 5 ml methanol and added dropwise to 100 ml ether. The yellow precipitate is filtered, washed with ether and dried to give the named compound; νmax (KBr) 1710, 1680 cm$^{-1}$.

C. N-Glycyl Amphotericin B

N-(N'-trifluoroacetylglycyl)amphotericin B (372 mg) in 13 ml 40% concentrated solution of ammonium hydroxide in dimethylformamide is stirred at room temperature with careful monitoring by thin layer chromatography (SiO$_2$ eluted with the lower phase of a 2:2:1 chloroform:methanol:water mixture). After 5 hours the mixture is reduced to half volume in vacuo, diluted with an equal volume of methanol and added dropwise to excess ether. The resulting yellow precipitate is filtered, triturated twice with ethanol and once with ether and dried to produce the named compound.

D. N-Glycyl Amphotericin B Methyl Ester

A solution of N-glycyl amphotericin B (75 mg) in 2 ml dimethylsulfoxide is treated with ethereal diazomethane. After evolution of nitrogen has ceased, the reaction is judged complete on the basis of thin layer chromatography (SiO$_2$ eluted with the lower phase of either a 2:2:1 chloroform:methanol:water or 1:1:1 chloroform:methanol:concentrated ammonium hydroxide mixture). The mixture is diluted with 2 ml methanol and added dropwise to excess water. The resulting yellow precipitate is filtered, washed with ether and dried to produce the named compound: νmax (KBr): 1710, 1660 cm$^{-1}$.

E. N-Glycyl Amphotericin B Methyl Ester Hydrochloride

To N-glycyl amphotericin B methyl ester dissolved in aqueous tetrahydrofuran (1:1) is added 0.1 N hydrochloric acid until a pH of 5 is reached. The solution is filtered through a 0.45μ micropore filter. The filtrate is lyophilized to yield the title compound: $[\alpha]_D^{26}-580°$ (H$_2$O); λmax (20% aqueous tetrahydrofuran) 367 nm ($E_{1\%}^1=800$), 387 nm ($E_{1\%}^1=1280$), 411 nm ($E_{1\%}^1=1430$).

EXAMPLE 3

N-D,L-Lysyl Amphotericin B Methyl Ester

A. N-(N',N''-Bis-Trifluoroacetyl-L-Lysyl)Amphotericin B

N,N'-bis-trifluoroacetyl-L-lysine is treated with N-hydroxysuccinimide according to Example 2A to obtain N,N'-bis-trifluoroacetyl-L-lysyloxy succinimide; $[\alpha]_D^{26}-31.4°$ (EtOH); νmax (KBr) 1810, 1790, 1740, 1700 cm$^{-1}$. This product (473 mg) is added under nitrogen to amphotericin B (500 mg) in 5 ml of a 9:1 dimethylsulfoxide:methanol mixture. After 3.5 hours, 6 ml of methanol is added and the mixture is added dropwise to excess ether. A fine, yellow precipitate is allowed to settle with cooling overnight. Filtration, washing with ether and drying gives the named compound: $[\alpha]_D^{26}+263.2$ (dimethylsulfoxide); νmax (KBr) 1710 cm$^{-1}$.

B. N-D,L-Lysyl Amphotericin B

N-(N',N''-bis-trifluoroacetyl-L-lysyl)amphotericin B (418 mg) in 30 ml of a 1:1 concentrated ammonium hydroxide:methanol mixture is stirred with careful monitoring by thin layer chromatography, (SiO$_2$ eluted with the lower phase of a 2:2:1 chloroform:methanol:water mixture). After 11.5 hours the mixture is added dropwise to excess ether. The yellow precipitate is filtered and washed successively with ethanol and ether, providing the named compound: $[\alpha]_D^{26}+293.4°$ (DMSO); νmax (KBr) 3400, 1710–1630 cm$^{-1}$; λmax (20% aqueous tetrahydrofuran), 348 nm ($E_{1\%}^1=340$), 367 nm ($E_{1\%}^1=750$), 386 nm ($E_{1\%}^1=1280$), and 410 nm ($E_{1\%}^1=1430$).

C. N-D,L-Lysyl Amphotericin B Methyl Ester

A solution of N-D,L-lysyl amphotericin B (319 mg) in 5 ml of dimethylsulfoxide under nitrogen is treated with an excess of etheral diazomethane. When a complete reaction is indicated by thin layer chromatography (SiO$_2$ eluted with the lower phase of a 1:1:1 chloroform:methanol:concentrated ammonium hydroxide mixture), the excess diazomethane is removed by a nitrogen stream and the resulting solution is diluted with 5 ml of methanol. Dropwise addition to excess ether yields a yellow precipitate which is filtered, washed with ether and dried to yield N-D,L-lysyl amphotericin B methyl ester; νmax (KBr) 1720 cm$^{-1}$; $[\alpha]_D^{26}+290.9$ (DMSO); λmax (20% aqueous tetrahydrofuran) 348 nm ($E_{1\%}^1=340$), 367 nm ($E_{1\%}^1=770$), 386 nm ($E_{1\%}^1=1300$), 410 nm ($E_{1\%}^1=1450$).

EXAMPLE 4

N-L-Lysyl Amphotericin B Methyl Ester

A. N,N'-Bis-Trichloroethoxycarbonyl-L-Lysyloxy Succinimide

To L-lysine (2.92 g) in 60 ml of methanol is added trichloroethyl-N-hydroxysuccinimidyl carbonate (14.55 g). The mixture is stirred overnight at room temperature, then treated with 2.5 ml concentrated ammonium hydroxide and stirred another 0.5 hour. The solvent is evaporated in vacuo and the residue is extracted with water and ethyl acetate. The organic layer is extracted successively with cold 5% HCl, water and brine solution, and then is dried over MgSO$_4$. Filtration and evaporation produces N,N'-bis-trichloroethoxycarbonyl-L-lysine as a glass. An analytical sample is prepared by two precipitations from chloroform/hexane; $[\alpha]_D^{26}$ −7.6° (EtOH); $\nu$max (KBr) 1720 cm$^{-1}$.

In a manner similar to Example 2A, utilizing anhydrous ethyl acetate as the solvent, N,N'-bis-trichloroethoxycarbonyl-L-lysine is reacted with N-hydroxy succinimide to obtain the above named compound; $[\alpha]_D^{26}$ −19.6° (EtOH); $\nu$max (KBr) 1820, 1785, 1715 cm$^{-1}$.

B. N-(N',N''-Bis-Trichloroethoxycarbonyl-L-Lysyl)Amphotericin B

To a stirred solution of amphotericin B (923 mg) in 10 ml dimethylsulfoxide and 1 ml of methanol under nitrogen is added 8.6 ml of a 0.21 M solution of the product of process step A in tetrahydrofuran. Sufficient dimethylsulfoxide is added to redissolve the precipitate fromed and the solution is stirred for 5 hours. Dilution with an equal volume of methanol and dropwise addition in 300 ml ether gives a yellow precipitate. Filtration, washing with ether and drying gives the named compound: $[\alpha]_D^{26}$ +198.0° (DMSO); $\lambda$max (KBr) 1720 cm$^{-1}$.

C. N-(L-Lysyl)Amphotericin B

To N-(N',N''-bis-trichloroethoxycarbonyl-L-lysyl) amphotericin B (1.04 g) in 40 ml of a 1:1 methanol:dimethylformamide mixture and (0.5 ml) acetic acid is added activated zinc dust (2.2 g). After 6.5 hours another 2.2 g zinc dust is added. After 8 hours the mixture is decanted into 500 ml ether. Filtration, washing with ether and drying gives a yellow powder. Chromatography on 135 g SiO$_2$ eluted with the lower phase of a 1:1:1 chloroform:methanol:concentrated ammonium hydroxide mixture produces the named compound: $\nu$max (KBr) broad, 3600–2250 cm$^{-1}$; 1690 cm$^{-1}$ broad; $\lambda$max (20% aqueous tetrahydrofuran), 348 nm ($E_{1\%}^1$=230), 367 nm ($E_{1\%}^1$=510), 386 nm ($E_{1\%}^1$=860) and 410 nm ($E_{1\%}^1$=930); $[\alpha]_D^{26}$ +225.9° (DMSO).

D. N-L-Lysyl Amphotericin B Methyl Ester

To N-L-lysyl amphotericin B (185 mg) in 10 ml of a 9:1 dimethylsulfoxide:methanol mixture is added excess etheral diazomethane. When a complete reaction is indicated by thin layer chromatography (SiO$_2$, 1:1:1 chloroform:methanol:concentrated ammonium hydroxide), the mixture is treated with one drop of a 1:1 acetic acid:methanol solution and diluted with 10 ml of methanol. The solution is added dropwise to excess ether which is filtered, collected, washed with ether and dried to yield the named compound: $\lambda$max (20% aqueous tetrahydrofuran) 348 nm ($E_{1\%}^1$=297), 367 nm ($E_{1\%}^1$=646), 386 nm ($E_{1\%}^1$=1095), 410 nm ($E_{1\%}^1$=1222).

EXAMPLE 5

N-D-Lysyl Amphotericin B Methyl Ester Dihydrochloride

A. N,N'-Bis-(9-Fluorenylmethyloxycarbonyl)-D-Lysine

To a stirred solution of D-lysine hydrochloride (4.5 g) in 175 ml of a sodium carbonate solution (10% in water):acetone (6:1) solution is added dropwise a solution of 9-fluorenylmethyl azidoformate in acetone (150 ml). After 16 hours the mixture is diluted with water and washed three times with hexane. The mixture is then acidified with concentrated hydrochloric acid and extracted three times with ethyl acetate. The ethyl acetate solution is washed successively with dilute hydrochloric acid, water, saturated sodium bicarbonate solution, and brine, dried over magnesium sulfate, then concentrated in vacuo to about 20 ml. The solution is added to hexane (1 l.) and the precipitate is collected and dried to afford the title compound: NMR (dimethylsulfoxide) $\delta$1.0–1.9 (m, 6H), 2.7–3.2 (m,2H), 3.8–4.7 (m,7H), 6.8–8.3 (m,19H).

B. N,N'-Bis-(9-Fluorenylmethyloxycarbonyl)-D-Lysyloxy Succinimide

To a stirred solution of N,N'-bis-(9-fluorenylmethyloxycarbonyl)-D-lysine (12.0 g) in 360 ml of an ethylacetate:dimethylformamide (35:1) mixture are added N-hydroxysuccinimide (3.1 g), 1-ethyl-3-(3-dimethylaminopropyl)carbodiimide hydrochloride (5.2 g) and diisopropylethylamine (2.0 ml). After 15 hours the solution is washed successively with dilute hydrochloric acid, water, saturated sodium bicarbonate solution, and brine, dried over magnesium sulfate, and concentrated in vacuo to about 20 ml. The solution is added to hexane (1 l.) and the precipitate is collected and dried to afford the title compound.

C. N-[N',N''-Bis-(9-Fluorenylmethyloxycarbonyl)-D-Lysyl] Amphotericin B

To a solution of N,N'-bis-(9-fluorenylmethyloxycarbonyl)-D-lysyloxy succinimide (0.60 g) in 22 ml of a dimethylformamide:dimethylsulfoxide:methanol (8:2:1) mixture is added amphotericin B (0.50 g). The solution is stirred at 40° for 2.5 hours, diluted with methanol (10 ml), and added to ether (500 ml). The yellow precipitate is filtered, washed with ether, and dried. Chromatography on SiO$_2$ (30 g) eluted with the lower phase of a 2:2:1 chloroform:methanol:water mixture produces the named compound.

D. N-[N',N''-Bis-(9-Fluorenylmethyloxycarbonyl)-D-Lysyl] Amphotericin B Methyl Ester To a stirred solution of N-[N',N''-bis-(9-fluorenylmethyloxycarbonyl)-D-lysyl]amphotericin B (1.4 g) in 55 ml of a dimethylsulfoxide:methanol (10:1) mixture are added methyliodide (1.6 ml) and diisopropylethylamine (1.2 ml). After 1 hour the solution is diluted with methanol (25 ml) and added to ether (1.5 l). The yellow precipitate is filtered and washed successively with ether, water, methanol:water (1:1) mixture, ether, and then dried to provide the title compound.

E. N-D-Lysyl Amphotericin B Methyl Ester Dihydrochloride

To a stirred solution of N-[N',N''-bis-(9-fluorenylmethyloxycarbonyl)-D-lysyl] amphotericin B methyl ester (1.2 g) in 50 ml of a dimethylsulfoxide:methanol (10:1) mixture is added 1,5-diazabicyclo[5.4.0]undec-5-ene (0.35 ml). After 0.5 hour the solution is diluted with methanol (25 ml) and added to ether (1 l.). The yellow precipitate is filtered, washed with ether, and dried. The yellow powder is suspended in water (100 ml) and 1.0 n-hydrochloric acid is added until a pH of 5.5 is reached. The solution is filtered through a 0.22μ micropore filter. The filtrate is lyophilized to afford the title compound: λmax (20% aqueous tetrahydrofuran) 348 nm ($E_{1\%}^1=278$), 367 nm ($E_{1\%}^1=608$), 387 nm ($E_{1\%}^1=1023$), 410 nm ($E_{1\%}^1=1146$).

EXAMPLE 6

N-Glycyl Derivative of the Polyene Macrolide Antibiotic 67-121-C

A. N-Iodoacetyl Derivative of the Polyene Macrolide Antibiotic 67-121-C 67-121-C (600 mg) is dissolved in 10 ml of a 9:1 dimethylsulfoxide:methanol mixture. This solution is chilled and to it iodoacetic anhydride (180 mg) is added. The reaction is stirred at room temperature. Completion of the reaction is checked by thin layer chromatography (chloroform-methanol-water 2:2:1 - lower phase). The resulting solution is diluted with an equal volume of methanol and added to vigorously stirred ether. The precipitate is filtered to yield the named compound.

B. N-Glycyl Derivative of the Polyene Macrolide Antibiotic 67-121-C

The product of step A is dissolved in a solution of dimethylformamide (10 ml) and concentrated ammonium hydroxide (28%; 3 ml). The reaction mixture is stirred for 2 hours and the volume is reduced to remove the aqueous ammonia. The residue is diluted with an equal volume of methanol and added to vigorously stirred ether. The precipitate is filtered and chromatographed on a silica gel column (chloroform:methanol:water (2:2:1)-lower phase) to obtain the title compound: $[\alpha]_D^{26}+117°$ (dimethylsulfoxide); λmax (20% aqueous tetrahydrofuran) 382 nm ($E_{1\%}^1=765$), 405 ($E_{1\%}^1=660$).

EXAMPLE 7

N-(β-Aminoethylglycyl)Amphotericin B Methyl Ester

To 30 ml of a 9:1 dimethylsulfoxide:methanol mixture and 2.46 ml of ethylenediamine is added N-iodoacetyl amphotericin B, which may be prepared in a manner similar to Example 6A, over 2.25 hours. The mixture is stirred 1.5 hours and then diluted with an equal volume of methanol. The solution is added to vigorously stirred 500 ml of ether. The precipitate is filtered and washed with ether to yield N-(β-aminoethylglycyl)amphotericin B. In a manner similar to that described in former Examples this compound can be transformed to the corresponding methylester: νmax (KBr) 1715 cm$^{-1}$; λmax (20% aqueous tetrahydrofuran) 348 nm ($E_{1\%}^1=296$), 367 nm ($E_{1\%}^1=639$), 386 nm ($E_{1\%}^1=1074$), 410 nm ($E_{1\%}^1=1167$).

EXAMPLE 8

Amphotericin B Propargyl Ester Hydrochloride

To a stirred solution of benzaldehyde (2.0 ml) in 22 ml of a 10:1 dimethylsulfoxide:methanol mixture is added amphotericin B (0.50 g). After 1 hour, diisopropylethylamine (1.0 ml) and propargyl bromide (1.0 ml of an 80% solution in toluene) are added. After 2 hours, 10 ml of methanol are added and the solution is added to 500 ml of ether. The precipitate is collected and washed successively with ether, water, methanol:water (1:1), and ether. The dried powder is suspended in water (40 ml) and 0.01 N-hydrochloric acid is added to a pH of 5. The solution is filtered through a 0.22μ micropore filter, and the filtrate is lyophilized to afford the title compound, λmax (20% aqueous tetrahydrofuran) 348 nm ($E_{1\%}^1=350$), 367 nm ($E_{1\%}^1=764$), 387 nm ($E_{1\%}^1=1290$), 410 nm ($E_{1\%}^1=1438$). In a manner analogous to those described above, other compounds of this invention can be prepared e.g. by treating amphotericin B, ascocin, aureofacin, aureofungin A, aureofungin B, candicidin, candidin, eurotin A, flavomycin, fulvomicin A, fulvomicin B, fulvomicin C, fungimycin, hamycin A, leucensomycin, levorin, mycoheptin, nystatin A, partricin, pimaricin, polyfungin, rimocidin, trichomycin A, vacidin A, DJ-400 B$_1$, DJ-400 B$_2$, 67-121A, 67-121B, 67-121C, PA 150, PA 616, 2814 H with the apropriate derivative of the desired amino compound such as glycine, lysine, glycylglycine, ornithine and ethanolamine or by transforming said polyene macrolide antibiotics into their respective N-iodoacetyl derivatives and reacting these derivatives with the apropriate amino compound such as ammonia, ethylenediamine and methylamine to obtain the respective N-glycyl, N-β-aminoethylglycyl or N-methylglycyl derivative of the relevant polyene macrolide antibiotic. Esters and acid addition salts of this invention are prepared according to known methods, especially according to the Examples.

The following compounds have been prepared accordingly;

N-D-lysyl-pimaricin methyl ester dihydrochloride, N-(2-aminoethoxycarbonyl)amphotericin B methyl ester; $[\alpha]_D^{26}+281.9$ (dimethylsulfoxide); λmax (20% aqueous tetrahydrofuran) 348 nm ($E_{1\%}^1=327$), 367 nm ($E_{1\%}^1=715$), 386 nm ($E_{1\%}^1=1206$), 410 nm ($E_{1\%}^1=1341$), N-β-alanyl amphotericin B methyl ester hydrochloride, N-L-histidyl amphotericin B methyl ester dihydrochloride, λmax (20% aqueous tetrahydrofuran): 348 nm ($E_{1\%}^1=257$), 367 nm ($E_{1\%}^1=556$), 387 nm ($E_{1\%}^1=935$), 410 nm ($E_{1\%}^1=1036$), N-D-tryptophyl amphotericin B methyl ester hydrochloride, λmax (20% aqueous tetrahydrofuran): 348 nm ($E_{1\%}^1=315$), 367 nm ($E_{1\%}^1=693$), 378 nm ($E_{1\%}^1=1145$), 410 nm ($E_{1\%}^1=1230$), N-D,L-2,3-diaminopropionyl amphotericin B methyl ester dihydrochloride, λmax (20% aqueous tetrahydrofuran): 348 nm ($E_{1\%}^1=304$), 367 nm ($E_{1\%}^1=668$), 387 nm ($E_{1\%}^1=1128$), 410 nm ($E_{1\%}^1=1264$), N-D,L-2,4-diaminobutyryl amphotericin B methyl ester dihydrochloride, λmax (20% aqueous tetrahydrofuran): 348 nm ($E_{1\%}^1=307$), 367 nm ($E_{1\%}^1=676$), 387 nm ($E_{1\%}^1=1148$), 410 nm ($E_{1\%}^1=1292$), N-D-2,4-diaminobutyryl amphotericin B methyl ester, N-L-2,4-diaminobutyryl amphotericin B methyl ester dihydrochloride, λmax (20% aqueous tetrahydrofuran): 348 nm ($E_{1\%}^1=319$ ), 367 nm ($E_{1\%}^1=702$), 387 nm ($E_{1\%}^1=1188$), 410 nm ($E_{1\%}^1=1340$), N-D,L-2,4-diaminobutyryl amphotericin B propargyl ester dihydrochloride, λmax (20% aqueous tetrahydrofuran): 348 nm ($E_{1\%}^1=294$), 367 nm ($E_{1\%}^1=635$), 387 nm ($E_{1\%}^1=1069$), 410 nm ($E_{1\%}^1=1192$), N-D,L-ornithyl amphotericin B hydrochloride, λmax (20% aqueous tetrahydrofuran) 366 nm ($E_{1\%}^1=740$), 386 nm ($E_{1\%}^1=1260$), 400 nm ($E_{1\%}^1=1400$), N-D,L-ornithyl amphotericin B methyl ester, λmax (20% aqueous tetrahydrofuran) 365 nm ($E_{1\%}^1=590$), 386 nm ($E_{1\%}^1=990$), 401 nm ($E_{1\%}^1=1100$), N-L-ornithyl amphotericin B methyl ester dihydrochloride, λmax (20% aqueous tetrahydrofuran): 348 nm ($E_{1\%}^1=300$), 367 nm ($E_{1\%}^1=667$), 387 nm ($E_{1\%}^1=1124$), 410 nm ($E_{1\%}^1=1251$), N-D-ornithyl amphotericin B methyl ester dihydrochloride, λmax (20% aqueous tetrahydrofuran): 348 nm ($E_{1\%}^1=315$), 367 nm ($E_{1\%}^1=692$), 387 nm ($E_{1\%}^1=1171$), 410 nm ($E_{1\%}^1=1312$), N-D-ornithyl amphotericin B propargyl ester dihydrochloride. λmax (20% aqueous tetrahydrofuran): 348 nm ($E_{1\%}^1=270$), 367 nm ($E_{1\%}^1=574$), 387 nm ($E_{1\%}^1=957$), 410 nm ($E_{1\%}^1=1054$), N-D-ornithyl amphotericin B (3-phenyl-2-propynyl)ester dihydrochloride, λmax (20% aqueous tetrahydrofuran): 348 nm ($E_{1\%}^1=254$), 367 nm ($E_{1\%}^1=540$), 387 nm ($E_{1\%}^1=905$), 410 nm ($E_{1\%}^1=986$), N-D-β-lysyl amphotericin B methyl ester dihydrochloride, λmax (20% aqueous tetrahydrofuran): 348 nm ($E_{1\%}^1=291$), 367 nm ($E_{1\%}^1=636$), 387 nm ($E_{1\%}^1=1075$), 410 nm ($E_{1\%}^1=1205$), N-L-β-lysyl amphotericin B methyl ester dihydrochloride, λmax (20% aqueous tetrahydrofuran): 348 nm ($E_{1\%}^1=290$), 367 nm ($E_{1\%}^1=640$), 387 nm ($E_{1\%}^1=1080$), 410 nm ($E_{1\%}^1=1205$), N-glycylglycyl amphotericin B, λmax (20% aqueous tetrahydrofuran) 367 nm ($E_{1\%}^1=760$), 386 nm ($E_{1\%}^1=1280$), 401 nm ($E_{1\%}^1=1430$), N-glycylglycyl amphotericin B methyl ester, λmax (20% aqueous tetrahydrofuran) 367 nm ($E_{1\%}^1=710$), 386 nm ($E_{1\%}^1=1200$), 401 nm ($E_{1\%}^1=1340$), N-(N',N''-diglycyl-D-lysyl) amphotericin B methyl ester dihydrochloride, λmax (20% aqueous tetrahydrofuran): 348 nm ($E_{1\%}^1=263$), 367 nm ($E_{1\%}^1=578$), 387 nm ($E_{1\%}^1=1012$), 410 nm ($E_{1\%}^1=1094$), N-D-lysyllysyl amphotericin B methyl ester amphotericin B allyl ester hydrochloride, λmax (20% aqueous tetrahydrofuran): 348 nm ($E_{1\%}^1=359$), 367 nm ($E_{1\%}^1=797$), 387 nm ($E_{1\%}^1=1352$), 410 nm ($E_{1\%}^1=1518$), amphotericin B-(3-phenyl-2-propynyl) ester hydrochloride, λmax (20% aqueous tetrahydrofuran): 348 nm ($E_{1\%}^1=269$), 367 nm ($E_{1\%}^1=559$), 387 nm ($E_{1\%}^1=919$), 410 nm ($E_{1\%}^1=1011$).

The following formulations exemplify the formulations in which the compounds of this invention can be used. The formulations are prepared by methods known in the art.

FORMULATIONS

| Formulation 1 Cream | mg/g |
|---|---|
| N-D-Ornithyl-amphotericin B methyl ester hydrochloride | 50.0 |
| white petrolatum | 150.0 |
| mineral oil | 60.0 |
| cetyl alcohol | 36.0 |
| stearyl alcohol | 36.0 |
| cetomacrogal 1000 | 22.0 |
| 4-chlor-m-cresol | 1.0 |
| purified water to make | 1 g. |

| Formulation 2 Ointment | mg/g |
|---|---|
| N-D-Ornithyl-amphotericin B methyl ester hydrochloride | 10.0 |
| propylene glycol | 100 |
| propylene glycol monostearate | 20.0 |
| white wax | 60.0 |
| white petrolatum, sufficient to make | 1 g. |

| Formulation 3 Lotion | mg/ml |
|---|---|
| N-D-Ornithyl-amphotericin B methyl ester hydrochloride | 50.0 |
| isopropyl myristate | 20.0 |
| glycerol stearate | 2.0 |
| promalgen 6 | 3.0 |
| propylene glycol | 15.0 |
| purified water, sufficient to make | 1 ml |

| Formulation 4 Aqueous Suspension for Intramuscular or Subcutaneous Injection | mg/ml |
|---|---|
| N-D-Ornithyl-amphotericin B methyl ester | 70.0–100.1 |
| polysorbate 80, USP | 0.5 |
| benzyl alcohol | 9.0 |
| sodium chloride | 5.0 |
| methylparaben | 1.3 |
| propylparaben | 0.2 |
| sodium carboxymethylcellulose | 5.0 |
| disodium edetate | 0.1 |
| polyethylene glycol | 20.0 |
| water for injection, sufficient to make | 1.0 ml. |

| Formulation 5 Intravenous Injection (Supplied as Sterile Lyophilized Powder) | mg/vial |
|---|---|
| N-D-Ornithyl-amphotericin B methyl ester hydrochloride | 40.0–60.0 |
| sodium desoxycholate | 70.0 |
| dibasic sodium phosphate (anhydrous) | 16.0 |
| monobasic sodium phosphate (anhydrous) | 9.0 |

| Formulation 6 Oral Suspension (to give a dose of 25 mg./5 ml.) | |
|---|---|
| N-D-Ornithyl-amphotericin B methyl ester hydrochloride | 5.00 g. |
| Magnesium Aluminum Silicate | 9.5 g. |
| Sodium carboxymethylcellulose, U.S.P. | 2.5 g. |
| Sodium Citrate, U.S.P. | 25.0 g. |
| Flavor | q.s. |
| Color | q.s. |
| Methylparaben, U.S.P. | 0.9 g. |
| Proylparaben, U.S.P. | 0.2 g |
| Polysorbate 80, U.S.P. | 1.0 g |
| Sorbitol Solution, U.S.P. | 500.0 g. |
| Water q.s. | 1000.0 g. |

Procedure:

1. Heat 200 ml. of water to boiling, and dissolve in it one half of the parabens. Cool to about 70° C., then mix in the Polysorbate 80. Sprinkle in the silicate, stirring until a uniform smooth suspension results.

2. Heat an additional 200 ml. of water to boiling, and dissolve in it the remainder of the parabens. Disperse the carboxymethylcellulose in this until a smooth gel results. Mix in the Sorbitol Solution. Then introduce and dissolve the sodium citrate.

3. Add 2 to 1 slowly, with constant stirring. Cool the mixture to 25° C. Add the N-D-ornithyl-amphotericin B methyl ester hydrochloride, flavor and color, mixing thoroughly. Add sufficient quantity of water to make the total volume 1000 ml.

I claim:

1. Derivatives of polyene macrolide antibiotics of the general formula

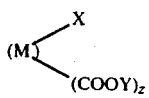

wherein M is a polyene macrolide antibiotic moiety containing an amino sugar moiety, the amino group of which is substituted by X, wherein X is

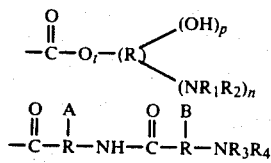

$-R_5$ or hydrogen, wherein A and B independently of each other are hydrogen or $NR_3R_4$ or one of A and B is hydrogen and the other is

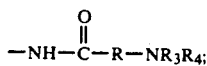

R is a saturated hydrocarbon group having 1 to 10 carbon atoms; $R_1$ and $R_2$ independently of each other are hydrogen or a straight chain alkyl group having 1 to 3 carbon atoms or one of $R_1$ and $R_2$ is hydrogen and the other a straight chain alkyl group having 1 to 3 carbon atoms substituted by an $NH_2$ group; $R_3$ and $R_4$ independently of each other are hydrogen or a straight chain alkyl group containing 1 to 3 carbon atoms; $R_5$ is histidyl, tyrosyl, tryptophyl, arginyl, phenylalanyl or prolyl or an $(\alpha)$-$N$-$[(NH_2)_m$-$R$-$CO]$— derivative of histidyl, tyrosyl, tryptophyl, phenylalanyl or prolyl; m is 1 or 2; n is 1 to 3, t is zero or 1, and when t is zero p is zero to 4 and when t is 1 p is zero; with the proviso that not more than one hetero atom is attached to the same carbon atom in any one of R, $R_1$ and $R_2$ and that in those compounds containing more than one R-group, these R-groups may be of the same or different chain length; z is zero or 1, and Y is hydrogen, an alkyl group containing 1 to 10 carbon atoms, allyl, propargyl, benzyl or phenylpropargyl, with the proviso that, when X is hydrogen, z must be 1 and Y must be allyl, propargyl, benzyl or phenylpropargyl; and the pharmaceutically acceptable acid addition salts of all the foregoing compounds.

2. A compound according to claim 1 which is derived from a polyene macrolide antibiotic of the general formula

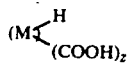

wherein z is zero or 1, which antibiotic of formula IV is amphotericin B, ascocin, aureofacin, aureofungin A, aureofungin B, candicidin, candidin, eurotin A, flavomycin, fulvomicin A, fulvomicin B, fulvomicin C, fungimycin, hamycin A, leucensomycin, levorin, mycoheptin, nystatin A, partricin, pimaricin, polyfungin, rimocidin, trichomycin A, vacidin A, DJ-400 $B_1$, DJ-400 $B_2$, 67-121A, 67-121B, 67-121C, PA 150, PA 616, or 2814 H.

3. A compound according to claim 1 wherein X is

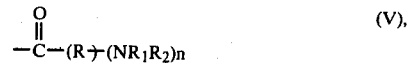

wherein n is 1 or 2 and R, $R_1$ and $R_2$ are as defined in claim 1.

4. A compound according to claim 1 wherein R is a saturated hydrocarbon group having 1 to 5 carbon atoms.

5. A compound according to claim 1 wherein $R_1$, $R_2$, $R_3$ and $R_4$ are hydrogen.

6. A compound according to claim 1 wherein X is lysyl or ornithyl.

7. A compound according to claim 1 wherein X is histidyl or tryptophyl.

8. A compound according to claim 1 wherein Y is an alkyl group containing 1 to 4 carbon atoms.

9. A compound according to claim 1 wherein X is hydrogen, z is one and Y is allyl, propargyl, benzyl or phenylpropargyl.

10. A compound according to claim 1 which is N-D-lysyl amphotericin B methyl ester dihydrochloride.

11. A compound according to claim 1 which is N-D-ornithyl amphotericin B methyl ester dihydrochloride.

12. A compound according to claim 1 which is N-D-lysyl pimaricin methyl ester dihydrochloride.

13. A compound according to claim 1 which is N-glycyl 67-121C.

14. A compound according to claim 1 which is N-glycyl amphotericin B methyl ester hydrochloride.

15. A compound according to claim 1 which is N-D-2,4-diaminobutyryl amphotericin B methyl ester dihydrochloride.

16. A compound according to claim 1 which is N-$\beta$-alanyl amphotericin B methyl ester hydrochloride.

17. A compound according to claim 1 which is N-(aminoethylglycyl) amphotericin B hydrochloride.

18. A compound according to claim 1 which is N-(aminoethylglycyl) amphotericin B methyl ester dihydrochloride.

19. A compound according to claim 1 which is N-D-lysyl amphotericin B hydrochloride.

20. A compound according to claim 1 which is N-L-lysyl amphotericin B hydrochloride.

21. A compound according to claim 1 which is N-L-lysyl amphotericin B methyl ester dihydrochloride.

22. A compound according to claim 1 which is N-L-ornithyl amphotericin B methyl ester dihydrochloride.

23. A compound according to claim 1 which is N-D-ornithyl amphotericin B propargyl ester dihydrochloride.

24. A compound according to claim 1 which is N-(2-aminoethoxycarbonyl) amphotericin B methyl ester hydrochloride.

25. A compound according to claim 1 which is N-L-histidyl amphotericin B methyl ester dihydrochloride.

26. A compound according to claim 9 which is amphotericin B allyl ester hydrochloride.

27. A compound according to claim 9 which is amphotericin B propargyl ester hydrochloride.

28. A compound according to claim 9 which is amphotericin B (3-phenyl-2-propynyl)ester hydrochloride.

29. The method for treating fungal infections which comprises administering to a mammal infected with a susceptible fungus, a non-toxic, fungicidally effective amount of a compound of claim 1.

30. A pharmaceutical composition comprising a non-toxic, fungicidally effective amount of a compound of claim 1 together with a non-toxic, pharmaceutically acceptable carrier.

* * * * *